United States Patent [19]

Toshiyasu et al.

[11] 4,103,008
[45] Jul. 25, 1978

[54] 7[2(2,3 DIOXOPIPERAZIN-1-YL-CARBONYLAMINO)SUBSTITUTED 2 PHENYLACETAMIDO]-3-2'-THIADIAZOLYL CEPHALOSPORANIC ACID DERIVATIVES

[76] Inventors: Ishimaru Toshiyasu, D-14, 2-7, Momoyamadai, Suita; Hatanaka Minoru, 2-11-25, Tenjincho, Takatsuki; Hatamura Mariko, 4-34, Zuikodori, Higashiyodogawa-ku, Osaka; Nitta Hazime, Towaso, 5-23-2, Izumicho, Suita, all of Japan

[21] Appl. No.: 781,834

[22] Filed: Mar. 28, 1977

[30] Foreign Application Priority Data

Apr. 7, 1976 [JP] Japan .................. 51-39549
Sep. 15, 1976 [JP] Japan ................. 51-111125

[51] Int. Cl.² ............... A61K 31/545; C07D 501/36
[52] U.S. Cl. ....................... 424/246; 544/27; 544/30; 544/26; 544/28; 544/385
[58] Field of Search ............... 544/27, 30; 424/246

[56] References Cited

U.S. PATENT DOCUMENTS

| 3,239,516 | 3/1966 | Heyningen et al. ............ 544/27 |
| 3,573,294 | 3/1971 | Long et al. ...................... 544/30 |

*Primary Examiner*—Donald G. Daus
*Assistant Examiner*—David E. Wheeler
*Attorney, Agent, or Firm*—Hubbell, Cohen, Stiefel & Gross

[57] ABSTRACT

Disclosed are broad spectrum antibiotics derived from 7-[D(−)-α-(4-alkyl-2,3-dioxopiperazin-1-yl-carbonylamino)-substitutedphenylacetamido]-3-(5-substituted or unsubstituted-1,3,4-thiadiazol-2-yl-thiomethyl)-3-cephem-4-carboxylic acids and salts thereof.

17 Claims, No Drawings

7[2(2,3 DIOXOPIPERAZIN-1-YL-CARBONYLAMINO)-SUBSTITUTED 2 PHENYLACETAMIDO]-3-2'-THIADIAZOLYL CEPHALOSPORANIC ACID DERIVATIVES

BACKGROUND OF THE INVENTION

This invention relates to new cephalosporin antibiotics, and in particular to 7-[D(−)-α-(4-alkyl-2,3-dioxopiperazin-1-yl-carbonylamino)-substituted phenylacetamido]-3-(5-substituted or unsubstituted-1,3,4-thiadiazol-2-yl-thiomethyl)-3-cephem-4-carboxylic acids and salts thereof, possessing high antibacterial action, especially against Pseudomonas strains of Gram negative bacteria.

There have heretofore been prepared numerous cephalosporin antibiotics, among which, cephalexin, cephaloridine, cefazolin, cephalothin and the like are commercially available and frequently used. However, these commercially available cephalosporins are not very effective against Psuedomonas strains. On the other hand, it is known, in the penicillin field, that for example, α-aminobenzylpenicillin whose α-amino group is substituted by 4-alkyl-2,3-dioxopiperazin-1-yl-carbonyl group is effective against Psuedomonas (Japanese Patent Provisional Publication No. 23284/1976).

SUMMARY OF THE INVENTION

According to the invention, there is provided a novel class of D(−) isomers of the compounds of formula (I):

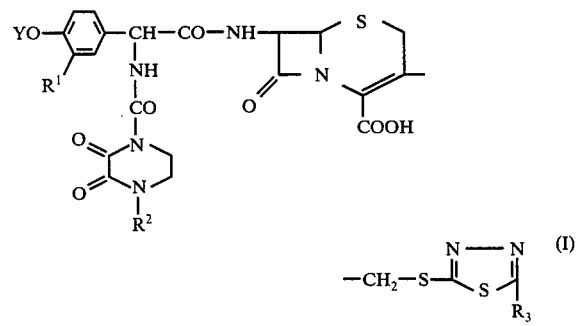

, wherein Y is hydrogen lower aliphatic acyl, lower alkoxycarbonyl or acetylmethylcarbonyl, $R^1$ is hydrogen or halogen, $R^2$ is lower alkyl and $R^3$ is hydrogen or lower alkyl; and pharmaceutically acceptable salts thereof, the invention also provides antibacterial compositions containing these compounds. In addition, the invention provides a method for the preparation of these compounds.

The D(−) isomers of the compounds of formula (I) exhibit high antibacterial action and possess the following characteristics (1) The antibacterial activity against pathogenic strains of Pseudomonas, Klebsiella, Vibrio and, Seratia and the like is the same or several times more potent than that of carbenicillin.

(2) They are effective against Penicillin-resistant strains and strains resistant to cephalothin or cefazolin.

(3) Some of the compounds show stronger antibacterial activities against the Gram negative bacteria, Escherichia coli or Salmonella strain than that of cefazolin.

(4) In animal infection test against Pseudomonas strain, some of the compounds showed an activity ten or more times greater than carbenicillin.

(5) Their toxicities including kidney toxicity are very low.

Because of these characteristics, the compounds of this invention are useful as medicines in the treatment or prevention of infectious diseases in mammals including humans.

The pharmaceutically acceptable salts of the D(−)-isomers of the compounds (I) include alkali metal salts such as the sodium or potassium salt, alkali earth metal salts such as the calcium, magnesium or zinc salt, basic amino acid salts such as lysine, arginine, ornithine or histidine salt and other salts with compounds which are capable of forming salts with cephalosporins and are conventionally employed in the art. Moreover, the compounds of this invention may exist either in the anhydrous or hydrated form, both of which should be understood to be included in the scope of the invention.

In the compounds of the Formula (I), wherein Y is lower aliphatic acyl, such group contains 2 − 5 carbon atoms and included therein are acetyl, propionyl, butyryl or iso-butyryl. Similarly, the term lower alkoxycarbonyl includes such groups containing 2 − 5 carbon atoms, such as methoxycarbonyl, ethoxycarbonyl, propoxycarbonyl, iso-propoxycarbonyl, butoxycarbonyl and iso-butoxycarbonyl. The halogen atom of $R^1$ may be chlorine, bromine or fluorine, preferably chlorine. The lower alkyl group of $R^2$ and $R^3$ contains 1 − 4 carbon atoms and is, e.g., methyl, ethyl, propyl, iso-propyl, butyl or iso-butyl.

A preferred group of the compounds of the invention are those of the formula:

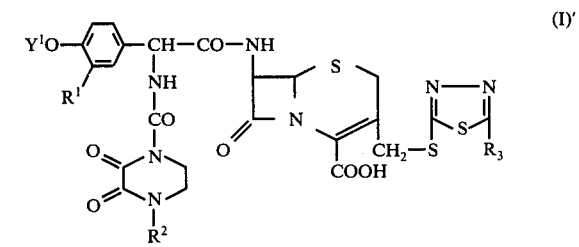

wherein $Y^1$ is the same as Y, with the exception of hydrogen and $R^1$, $R^2$ and $R^3$ are as defined above in formula (I).

A further preferred group comprises the compounds of the formula (I)' wherein $Y^1$ is lower alkoxycarbonyl or lower aliphatic acyl group, $R^1$ is hydrogen or chlorine, $R^2$ is ethyl and $R^3$ is hydrogen.

The most preferred group comprises the compounds of the formula (I)' wherein $Y^1$ is ethoxycarbonyl, $R^1$ is hydrogen or chlorine, $R^2$ is ethyl and $R^3$ is hydrogen.

Another preferred group of the compounds in the invention is the compounds of the formula (I) wherein Y is hydrogen.

More specifically, the most preferred compounds of the invention are the following:

7-[D(−)-α-(4-methyl(or ethyl or propyl)-2,3-dioxopiperazin-1-yl-carbonylamino)-p-ethoxycarbonyloxy(or propoxycarbonyloxy or butoxycarbonyloxy)phenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-p-acetoxy(or propionyloxy)phenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-p-acetoacetoxyphenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-p-hydroxy-phenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-m-chloro-p-ethoxycarbonyloxy(or propoxycarbonyloxy or butoxycarbonyloxy)phenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-m-chloro-p-acetoxy(or propionyloxy)phenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-m-chloro-p-acetoacetoxyphenylacetamido]-3-(5-methyl(or hydrogen)-1,3,4-thiadiazol-2-yl-thiomethyl)-3-cephem-4-carboxylic acid;

7-[D(—)-α-(4-methyl(or ethyl or propyl)-2,3-dioxo-piperazin-1-yl-carbonylamino)-m-chloro-p-hydroxyphenylacetamido]-3-(5-methyl(or hydrogen)-1,3,4-thiadiazol-2-yl-thiomethyl)-3-cephem-4-carboxylic acid;

and alkali metal (e.g., sodium or potassium) salts thereof.

The compounds of the invention can be prepared, for example, by the steps of:

(a) reacting a 3-substituted-7-aminocephalosporanic acid of the formula (II):

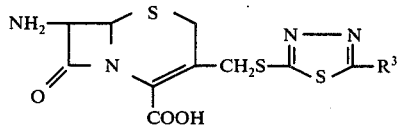

(II)

wherein $R^3$ is as defined above, or its salt, mixed anhydride with an organic silyl compound or phosphorus compound or easily hydrolyzable ester; with a reactive derivative of a D-(—) compound of the formula (III):

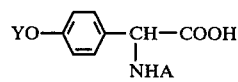

(III)

wherein Y and $R^1$ are as defined above, and A is a protecting group for the amino group, removing the protecting group, reacting the resultant compound with a reactive derivative of 4-alkyl-2,3-dioxo-piperazin-1-yl-carboxylic acid, or (b) reacting a 3-substituted-7-aminocephalosporanic acid of formula (II), or its salt, mixed anhydride or easily hydrolyzable ester, with a reactive derivative of D (—)-α-(4-alkyl-2,3-dioxopiperazin-1-yl-carbonylamino)-m-substituted(or unsubstituted)-p-hydroxy(or substituted hydroxy)phenylacetic acid of the formula (III)′:

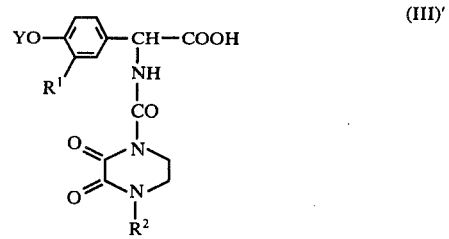

(III)′ wherein Y, $R^1$ and $R^2$ are the same meaning as defined above, (c) reacting 7-aminocephalosporanic acid or its salt, mixed anhydride or easily hydrolyzable ester, with a reactive derivative of the formula (III) followed by the removal of the protecting group and the reaction with a reactive derivative of a 4-alkyl-2,3-dioxopiperazin-1-yl-carboxylic acid or with a reactive derivative of the formula (III)′, and then reacting the resulting cephalosporin compound with 1,3,4-thiadiazol-2-thiol(or its 5-lower alkyl substituent) or a salt thereof, or (d) reacting a D-(—) compound of the formula (IV):

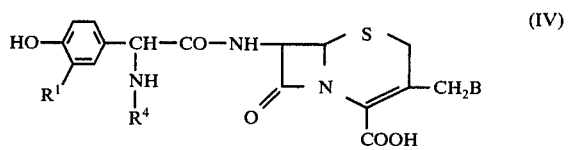

(IV)

wherein $R^1$ is as defined above, $R^4$ is a protecting group for the amino group or a 4-alkyl-2,3-dioxopiperazin-1-yl-carbonyl group, B is an acyloxy group or a group of the formula:

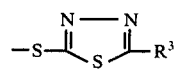

in which $R^3$ is as defined above, with an acylating agent of the formula (V): Y–X wherein Y is as defined above and X is a reactive leaving group, to give the acylated hydroxy compound, and then if necessary converting the $R^4$ protecting group into a 4-alkyl-2,3-dioxopiperazin-1-yl-carbonyl group or converting the acyloxy group B into a group B of the formula:

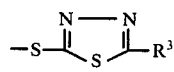

in which $R^3$ is as defined above, and then if necessary, hydrolyzing or acidifying the resultant cephalosporin to give the corresponding free carboxylic acid of the formula (I) and/or treating the free carboxylic acid of the formula (I) with a base to give the corresponding pharmaceutically acceptable salt.

The reactions described above can be divided basically into (1) the acylation of 7-amino group of the cephalosporanic acids, (2) the acylation of the α-amino group on the side chain of cephalosporin compounds, (3) the acylation of the p-hydroxy group on the side chain and (4) the substitution reaction of the 3-position of cephalosporin compounds.

The reactive derivatives of the acylating agents used for these reactions are preferably the acid halide, mixed anhydride or active ester. Especially, the acylating agent of the formula (V), i.e., Y–X is preferably an acid halide such as a lower alkoxycarbonyl halide or a lower aliphatic acid halide, or the acid anhydride but includes dimethylketene, ketene or diketene which are usable for specific groups.

The easily hydrolyzable esters of 3-substituted-7-aminocephalosporanic acid of the formula (II) are preferably the acid esters such as the 2-oxo-4-methoxycarbonyloxy-butan-3-yl ester, 2,4-dioxo-pentan-3-yl ester and like esters which have been discovered by one of the inventors hereof.

Such esters can be readily hydrolyzed by treatment with sodium nitrite or like compounds under neutral or weak acidic conditions, to give the corresponding free acid without causing β-lactam-decomposition and in a high yield.

Examples of the protecting group for the amino group there are included t-butoxycarbonyl, haloacetyl, formyl, benzyloxycarbonyl, 1-N,N-dimethylaminocarbonylpropen-2-yl, 1-N-morpholino-carbonylpropen-2-yl, 1-methoxycarbonylpropen-2-yl group and the like.

Moreover, when Y in formula (II) is acetyl, propionyl, butyryl, ethoxycarbonyl, propoxycarbonyl or a like group, the desired reaction(s) may be carried out by the use of an acid halide compound having a protonated amino group (e.g., amino salt with a mineral acid, organic sulfonic acid, halogenated aliphatic acid or like compound) as the protected amino group.

The solvent used for the above reactions may be aqueous solvents such as aqueous acetone, dioxane, acetonitrile, dimethylformamide, ethyl acetate, methylene chloride or chloroform, or anhydrous inert organic solvents such as methylene chloride, ethylene chloride, chloroform, dioxane, dimethylformamide or tetrahydrofuran.

In the above reactions, the kinds of reactive derivatives of the acylating agents, easily hydrolyzable esters or mixed anhydrides of 3-substituted-7-aminocephalosphoranic acids, protecting groups for amino group, inert solvents and like materials, and the reaction conditions (e.g., pH, reaction temperature), reaction means and the like may be suitably selected and utilized from those known in the art.

Biological Activity

Given below are the test results of in vitro antibacterial activity studies, serum concentrations and accumulative urinary excretions in rabbits and the protecting effects in mice, of some representative compounds of the invention.

The compounds used in the tests are shown in the following Table 1, but all of these compounds are in the form of the sodium salt.

Table 1

| COMPOUND No. | IN THE FORMULA (I) | | | |
|---|---|---|---|---|
| | Y | $R_1$ | $R_2$ | $R_3$ |
| I | H | H | $C_2H_5$ | H |
| II | H | Cl | $C_2H_5$ | H |
| III | $CH_3CO-$ | H | $C_2H_5$ | H |
| IV | $CH_3CO-$ | Cl | " | " |
| V | $C_2H_5OCO-$ | H | " | " |
| VI | $C_2H_5OCO-$ | Cl | " | " |

The compounds used for comparison purposes:
C: sodium 6-[D(−)-α-(4-ethyl-2,3-dioxopiperazin-1-yl-carbonylamino)phenylacetamido]penicillanate
CB-PC: sodium carbenicillin
CEX: sodium cephalexin
CEZ: sodium cefazolin Table 2

| Compound Organism | IN VITRO MIC (meg/ml) | | | | | | | | | |
|---|---|---|---|---|---|---|---|---|---|---|
| | I | II | III | IV | V | VI | C | CB-PC | CEX | CEZ |
| Staphylococcus aureus FDA 209NIH, P-J C-1 | 0.39 | 0.20 | 12.5 | 6.25 | 0.39 | 0.39 | 0.78 | 0.20 | 0.78 | 0.05> |
| Streptococcus faecalis ATCC 8043 | 0.78 | 1.56 | 1.56 | 1.56 | 12.5 | 6.25 | 12.5 | 6.25 | 50 | 2.5 |
| Bacillus substilis ATCC 6633 | 0.78 | 0.39 | 12.5 | 6.25 | 0.78 | 0.39 | 0.39 | 0.05> | 0.39 | 0.05> |
| Escherichia coli C 73-1 | 1.56 | 1.56 | 3.13 | 6.25 | 1.56 | 1.56 | 3.13 | 100< | 25 | 3.13 |
| Escherichia coli C 73-4 | 0.39 | 1.56 | 3.13 | 6.25 | 3.13 | 3.13 | 6.25 | 6.25 | 6.25 | 0.78 |
| Salmonella enteritidis No. 11 | 0.05> | 0.05> | 1.56 | 3.13 | 0.2 | 0.2 | 0.05> | 0.39 | 3.13 | 0.78 |
| Salmonella strain C73-1 | 0.39 | 0.78 | 0.78 | 1.56 | 1.56 | 3.13 | 6.25 | 6.25 | 3.13 | 0.78 |
| Salmonella strain C 73-30 | 0.39 | 1.56 | 0.78 | 1.56 | 1.56 | 3.13 | 6.25 | 6.25 | 3.13 | 0.78 |
| Shigella dysenteriae shigae | 0.05> | 0.05> | 0.78 | 0.39 | 0.78 | 1.56 | 0.20 | 0.78 | 1.56 | 0.78 |
| Klebsilla pneumoniae | 0.10 | 0.78 | 0.78 | 0.78 | 0.39 | 1.56 | 3.13 | 6.25 | 3.13 | 0.78 |
| Proteus morganii kono | 1.56 | 3.13 | 6.25 | 3.13 | 3.13 | 3.13 | 0.78 | 0.39 | 100< | 100< |
| Proteus morganii C73-23 | 6.25 | 6.25 | 12.5 | 12.5 | 12.5 | 12.5 | 3.13 | 1.56 | 100< | 100< |
| Enterobacter strain C73-17 | 25 | 12.5 | 25 | 25 | 3.13 | 1.56 | 6.25 | 25 | 100 | 25 |
| Serratia strain No. 1 | 3.13 | 3.13 | 6.25 | 3.13 | 3.13 | 6.25 | 3.13 | 3.13 | 100< | 100< |
| Serratia strain No. 2 | 3.13 | 6.25 | 1.56 | 3.13 | 3.13 | 6.25 | 3.13 | 3.13 | 100< | 100< |
| Pseudomonas aeruginosa C73-2 | 6.25 | 6.25 | 1.56 | 3.13 | 6.25 | 12.5 | 6.25 | 25 | 100< | 100< |
| Pseudomonas strain C73-63 | 1.56 | 1.56 | 6.25 | 3.13 | 6.25 | 3.13 | 3.13 | 12.5 | 100< | 100< |
| Pseudomonas strain C73-83 | 25 | 12.5 | 25 | 25 | 25 | 12.5 | 50 | 100< | 100< | 100< |
| Vibrio parahaemolyticus K - 3 | 6.25 | 12.5 | 6.25 | 12.5 | 6.25 | 12.5 | 25 | 100< | 6.25 | 1.56 |
| Vibrio parahaemolyticus K - 5 | 6.25 | 12.5 | 6.25 | 12.5 | 6.25 | 12.5 | 12.5 | 100< | 50 | 12.5 |

Table 3
SERUM CONCENTRATION AND ACCUMULATIVE URINARY EXCRETION IN RABBIT

| COMPOUND | SERUM CONCENTRATION mcg/ml, after 30 mins. | ACCUMULATIVE URINARY EXCRETION %, after 6 hrs. |
|---|---|---|
| I | 52.8 | 33.4 |
| II | 28.8 | 24.0 |
| III | 62.0 | 48.0 |
| IV | 34.9 | 27.0 |
| V | 43.0 | 24.1 |
| VI | 19.4 | 17.4 |

Each of the test compounds (20 mg/kg) was intramuscularly administered to one group of 3 rabbits, and the amounts of antibiotics were measured by a conventional method, using Sarcina lutea.

Table 4
$ED_{50}$ IN PSEUDOMONAS INFECTION IN MICE

| COMPOUND | $ED_{50}$ mg/mouse | COMPOUND | $ED_{50}$ |
|---|---|---|---|
| I | 3.0 | V | 1.0 |
| II | 2.2 | VI | 0.8 |
| III | 2.6 | CB-PC | 8.1 |
| IV | 1.8 | | |

Pseudomonas aerugenosa E 2 strain (3.6 × 10$^4$) was intraperitonealy injected to each group of 10 of ICR-JCL mouse (male, 20g). After 2 hrs., each of the test compounds was intramuscularly administered to the infected mice and the $ED_{50}$ values were measured after 7 days.

The compounds of the invention can be used in the treatment or prevention of infectious diseases in mammals including humans.

According to one aspect of the invention, there are provided pharmaceutical compositions comprising a compound of the formula (I) and a pharmaceutically acceptable carrier therefor.

The compounds of the invention, normally between 100 mg and 1,500 mg, preferably between 250 mg and 1,000 mg as a unit dosage for adult, will be administered 4 – 6 times per day, usually in non-oral form, but occasionally in oral form in the treatment of human bacterial infectious diseases.

The pharmaceutical composition which can be used for the above administration comprises a compound of the invention and a pharmaceutically acceptable carrier in solid or liquid form. The compositions are formulated in solid preparations such as tablets, capsules, powders, reconstitutable powders and the like, or in liquid preparations such as injections, suspensions, syrups and the like. The solid or liquid carriers may be those which are known in the art. In addition, it is preferred to formulate the preparations so as to contain the active ingredient in the amount necessary for a unit dosage as mentioned above.

The following examples are provided solely for the purpose of illustration and are not to be construed as limitations of this invention, many variations of which are possible without departing from the spirit or scope thereof.

EXAMPLE 1

7-[D(—)-α-(4-ethyl-2,3-dioxopiperazin-1-yl-carbonylamino)-m-chloro-p-hydroxyphenylacetamido]-3-(1,3,4-thiadiazol-2-yl-thiomethyl)-3-cephem-4-carboxylic acid:

To a solution of 135 mg (0.35 m mole) of D(—)-α-(4-ethyl-2,3-dioxopiperazin-1-yl-carbonylamino)-m-chloro-p-hydroxyphenylacetic acid in 5 ml of tetrahydrofuran there was added 0.37 ml of a solution of 1N N-methylmorpholine-tetrahydrofuran which was then cooled to −20° C. To this solution was added 0.37 ml of a solution of 1 M ethyl chloroformate-tetrahydrofuran under stirring, followed by the reaction at −20° − −10° C for about 90 minutes to give the mixed anhydride.

Separately, 116 mg of 7-amino-3-(1,3,4-thiadiazol-2-yl-thiomethyl)-3-cephem-4-carboxylic acid were suspended in 3 ml of methylene chloride and allowed to react with 0.12 ml of N,O-bistrimethylsilyl-acetamide at 0° − 5° C to obtain a clear solution, which was added dropwise to the above mixed anhydride solution below −20° C.

After stirring the solution at −20° − −15° C overnight, the solvent was removed under reduced pressure. To the residue were added 10 ml of ice-water and 30 ml of ethyl acetate and the mixture was adjusted to pH2.0 with a dilute hydrochloric acid solution under stirring. The organic layer was separated, washed with aqueous sodium chloride, dried and the solvent was evaporated under reduced pressure. The residue was dissolved in a small amount of acetone and treated with an aqueous concentrated sodium acetate solution in accordance with the usual method to obtain the desired sodium salt. The yield of the product was 83%. The free acid was obtained by dissolving the sodium salt in a small amount of water, adding ethyl acetate to the solution, followed by adjustment to pH 2.0 with a dilute hydrochloric acid solution to separate the organic layer, washing same with aqueous sodium chloride, drying and removing the solvent under reduced pressure.

mp 159° – 164° C (decomp.)
IR(Nujol) $\nu c=o$: 1780, 1730 – 1660 cm$^{-1}$
UV(ethanol) λmax.: 234, 271 nm.

EXAMPLE 2

Sodium 7-[D(—)-α-(4-ethyl-2,3-dioxopiperazin-1-yl-carbonylamino)-p-hydroxyphenylacetamido]-3-(1,3,4-thiadiazol-2-yl-thiomethyl)-3-cephem-4-carboxylate:

Instead of the D(—)-α-(4-ethyl-2,3-dioxopiperazin-1-yl-carbonylamino)-m-chloro-p-hydroxyphenylacetic acid used in Example 1, D(—)-α-(4-ethyl-2,3-dioxopiperazin-1-yl-carbonylamino)-p-hydroxyphenylacetic acid was used and treated in a similar manner that of Example 1.

The above-named sodium salt was obtained in 78% yield.

IR (KBr): 1780 cm$^{-1}$
UV (ethanol) λmax: 233, 270 nm.

EXAMPLE 3

7-[D(—)-α-(4-ethyl-2,3-dioxopiperazin-1-yl-carbonylamino)-p-acetoxyphenylacetamido]-3-(1,3,4-thiadiazol-2-yl-thiomethyl)-3-cephem-4-carboxylic acid:

10.45 g (20 m mol.) of 7-[D(—)-α-amino-p-acetoxyphenylacetamido]-3-(1,3,4-thiadiazol-2-yl-thiomethyl)-3-cephem-4-carboxylic acid which was obtained by the removal of the t-butoxycarbonyl group of 7-[D(—)-α-t-butoxycarbonylamino-p-acetoxyphenylacetamido]-3-(1,3,4-thiadiazol-2-yl-thiomethyl)-3-cephem-4-carboxylic acid [mp 178° – 182° C (decomp.)] by a conventional method, were suspended in 150 ml of 80% aqueous acetone at 0° C. To the suspension there was added dropwise an anhydrous tetrahydrofuran solution containing 5.3 g (26 m mol.) of 4-ethyl-2,3-dioxopiperazin-1-yl-carbonylchloride, with the pH being maintained at 7.5 – 8.2 by the dropwise addition of triethylamine. The reaction was monitored by thin layer chromatography (acetic acid:n-butanol:water = 4:1:1, sprayed with a solution of iodo azide, then heated and colored). After the addition was completed, the reaction mixture was stirred for 30 minutes under ice-cooling to obtain a homogeneous solution, to which 50 ml of ether and 50 ml of ice-water were added. An aqueous layer was separated, adjusted to pH 2.8 with 20% aqueous phosphoric acid and then the acetone was removed under reduced pressure. The precipitated crystals were collected, washed with water and then dried. The product was treated with a small amount of ethyl acetate and dried [11.3 g (82%)]. Then the ethyl acetate solution and aqueous solution were combined and sodium chloride was added to the mixture followed by extraction with ethyl acetate. The ethyl acetate layer was washed with aqueous sodium chloride, dried and then the solvent was removed under reduced pressure. The residue was treated with a small amount of ethyl acetate and the resulting solid was collected [1.1g (8%)].

12.4g (90%) of the object compound was obtained.
mp 169° – 172° C (decomp.)
IR (KBr): 1780 ($\beta$-lactam), 1720 – 1650 cm$^{-1}$
UV $\lambda$max: 264 nm. (methanol)
TLC (acetic acid:n-butanol:water = 4:1:1):
Rf = 0.23

The corresponding sodium or potassium salt was obtained by dissolving the free acid in acetone and isopropyl alcohol, adding a calculated amount of an aqueous saturated sodium acetate or potassium acetate solution to the solution and treating same in a conventional manner.

EXAMPLE 4

7-[D(−)-α-(4-ethyl-2,3-dioxopiperazin-1-yl-carbonylamino)-m-chloro-p-acetoxyphenylacetamido]-3-(1,3,4-thiadiazol-2-yl-thiomethyl)-3-cephem-4-carboxylic acid:

Instead of 7-[D(−)-α-amino-p-acetoxyphenylacetamido]-3-(1,3,4-thiadiazol-2-yl-thiomethyl)-3-cephem-4-carboxylic acid used in Example 3, 7-[D(−)-α-amino-m-chloro-p-acetoxyphenylacetamido]-3-(1,3,4-thiadiazol-2-yl-thiomethyl)-3-cephem-4-carboxylic acid obtained from 7-[D(−)-α-t-butoxycarbonylamino-m-chloro-p-acetoxyphenylacetamido]-3-(1,3,4-thiadiazol-2-yl-thiomethyl)-3-cephem-4-carboxylic acid (mp 143° – 148° C (decomp.)] in a conventional manner was used and treated in a manner similar to that of Example 1.

The object compound was obtained in 88% yield.
mp 143° – 146° C (decomp.)
IR (KBr): 1780 ($\beta$-lactam), 1720 – 1650 cm$^{-1}$
UV $\lambda$max: 265 nm.

EXAMPLE 5

7-[D(−)-α-(4-ethyl-2,3-dioxopiperazin-1-yl-carbonylamino)-p-ethoxycarbonyloxyphenylacetamido]-3-(1,3,4-thiadiazol-2-yl-thiomethyl)-3-cephem-4-carboxylic acid:

(a) 7-[D(−)-α-(t-butoxycarbonylamino)-p-hydroxyphenylacetamido]-cephalosporanic acid:

5.34g (20 m mol.) of α-(t-butoxycarbonylamino)-p-hydroxyphenylacetic acid [mp 118° – 120° C (decomp.)] were dissolved in 25 ml of anhydrous tetrahydrofuran and cooled to −20° C. To this solution, there were added 2.22g (22 m mol.) of N-methylmorpholine to yield the N-methylmorpholine salt (mp 70° – 74° C (decomp.)]. 2.21g (20.4 m mol.) of ethyl chlorocarbonate were added to the suspension of the N-methylmorpholine salt, and the mixture was stirred for 1.5 hrs. at −20° C and then cooled to −50° C.

Separately 5.67g (20 m mol. purity: 96%) of 7-aminocephalosporanic acid (7-ACA) were dissolved in 25 ml of methanol containing 2.63g (26 m mol.) of triethylamine and diluted with 25 ml of methylene chloride. The solution was added dropwise to the above mixed anhydride solution, and the mixture was stirred for 2 hrs. at below-40° C and then the temperature was allowed to gradually rise. The reaction was monitored by thin layer chromatography (ethyl acetate:methanol:acetic acid = 8:1:1, Rf = 0.55). After the reaction was complete, the reaction mixture was evaporated under reduced pressure. To the residue there was added a mixture of water and ethyl acetate and the pH was adjusted to 7.5. The aqueous layer was washed with ethyl acetate, and then adjusted to pH 3.0 with citric acid, extracted with ethyl acetate, dried and evaporated under reduced pressure to give the object compound as an oil (yield: 95%). It was triturated in iso-propyl ether to yield a solid (yield: 80%).

7-[D(−)-α-(t-butoxycarbonylamino)-p-hydroxyphenylacetamido]-3-(1,3,4-thiadiazol-2-yl-thiomethyl)-3-cephem-4-carboxylic acid:

2.08g (4 m mol.) of α-(t-butoxycarbonylamino)-p-hydroxyphenylacetamido]-cephalosporanic acid, 0.74g (8.8 m mol.) of sodium bicarbonate and 0.52g (4.4 m mol.) of 1,3,4-thiadiazol-2-thiol were dissolved in 30 ml of a phosphate buffer solution and the mixture was heated to 70° C at pH 6.5 – 6.8 with stirring. The reaction was monitored by thin layer chromatography (ethyl acetate:benzene:acetic acid = 32:8:5, Rf = 0.16). After about 4 hrs., the reaction solution was washed with ethyl acetate. To the aqueous layer there was added ethyl acetate and then the mixture was adjusted to pH 3.0 and extracted with ethyl acetate. The ethyl acetate layer was dried and evaporated under reduced pressure to give an oil which was solidified by trituration in ether (yield: 2.09g 90%). This compound was further purified by column chromatography using chloroform:methanol = 10:1 as the eluent.

(c) 7-[D(−)-α-(t-butoxycarbonylamino)-p-ethoxycarbonyloxyphenylacetamido]-3-(1,3,4-thiadiazol-2-yl-thiomethyl)-3-cephem-4-carboxylic acid:

2.32g (4 m mol.) of 7-[D(−)-α-(t-butoxycarbonylamino)-p-hydroxyphenylacetamido]-3-(1,3,4-thiadiazol-2-yl-thiomethyl)-3-cephem-4-carboxylic acid were suspended in 20 ml of anhydrous methylene chloride under ice-cooling and 0.89g (8.8 m mol.) of triethylamine was added to obtain a clear solution, to which was added dropwise an anhydrous methylene chloride solution containing 0.48g (4.4 m mol.) of ethyl chlorocarbonate. The reaction was monitored by thin layer chromatography. (ethyl acetate:benzene:acetic acid = 32:8:5, Rf = 0.23) After the reaction was complete, the reaction mixture was evaporated under reduced pressure. The residue was dissolved in a mixture of ethyl acetate and water under ice-cooling, and then the mixture was adjusted to pH 8.0 – 8.5 with sodium bicarbonate. The aqueous layer was separated, adjusted to pH 3.0 with citric acid and extracted with ethyl acetate. The ethyl acetate layer was washed with water, dried with magnesium sulfate and evaporated under reduced pressure to give an oil which was solidified by trituration in ether and petroleum ether. (yield: 1.89g, 72.7%).
mp 156° – 157° C (decomp.)

IR (Nujol): 1780 cm$^{-1}$
UV λmax: 273 nm. (ethanol)

(d) 7-[D(—)-α-amino-p-ethoxycarbonyloxyphenylacetamido]-3-(1,3,4-thiadiazol-2-yl-thiomethyl)-3-cephem-4-carboxylic acid trifluoro acetate:

1.89g (2.9 m mol.) of the compound obtained in c), above, were dissolved in 3.1 ml of anisole and 9.5 ml of trifluoroacetic acid with stirring under ice-cooling. The stirring was continued for 1 hr. After the reaction was complete, the mixture was evaporated under reduced pressure and triturated in ether to give the object compound as a solid in quantitative yield.

mp 147° - 149° C (decomp.)
IR (Nujol): 1770 cm$^{-1}$
UV λmax: 267 nm. (ethanol)

(e) 7-[D(—)-α-(4-ethyl-2,3-dioxopiperazin-1-yl-carbonylamino)-p-ethoxycarbonyloxyphenylacetamido]-3-(1,3,4-thiadiazol-2-yl-thiomethyl)-3-cephem-4-carboxylic acid:

0.2g (0.286 m mol.) of the trifluoroacetate obtained above was dissolved in 10 ml of an aqueous 80% acetone solution, to which was added 0.1 ml of triethylamine under ice-cooling. The solution was adjusted to pH 8.0 with sodium bicarbonate followed by the dropwise addition an acetone solution containing 0.08g of 4-ethyl-2,3-dioxopiperazin-1-yl-carbonyl chloride. The reaction was monitored by thin layer chromatography. (n-butanol:acetic acid:water = 4:1:1, Rf = 0.25). After the reaction was complete, the reaction mixture was extracted with ethyl acetate at pH 3.0, washed with water, dried with magnesium sulfate and evaporated under reduced pressure to give the object compound as a solid in a 91% yield.

mp 153° - 159° C (decomp.)
IR (KBr): 1780 (β-lactam), 1720 - 1650 cm$^{-1}$
UV λmax: 264 nm. (methanol)

EXAMPLE 6

7-[D(—)-α-(4-ethyl-2,3-dioxopiperazin-1-yl-carbonylamino)-m-chloro-p-ethoxycarbonyloxyphenylacetamido]-3-(1,3,4-thiadiazol-2-yl-thiomethyl)-3-cephem-4-carboxylic acid:

Instead of α-(t-butoxycarbonylamino)-p-hydroxyphenylacetic acid used in Example 5, α-(t-butoxycarbonylamino)-m-chloro-p-hydroxyphenylacetic acid was used and treated in a similar manner to that of Example 5. The compound corresponding to each step in Example 5 was obtained.

(a) 7-[D(—)-α-(t-butoxycarbonylamino)-m-chloro-p-hydroxyphenylacetamido]-cephalosporanic acid was obtained as an oil.

(b) 7-[D(—)-α-(t-butoxycarbonylamino)-m-chloro-p-hydroxyphenylacetamido]-3-(1,3,4-thiadiazol-2-yl-thiomethyl)-3-cephem-4-carboxylic acid.
mp 182° C (decomp.)
IR (Nujol): 1780 cm$^{-1}$
UV λmax: 275 nm. (ethanol)

(c) 7-[D(—)-α-(t-butoxycarbonylamino)-m-chloro-p-ethoxycarbonyloxyphenylacetamido]-3-(1,3,4-thiadiazol-2-yl-thiomethyl)-3-cephem-4-carboxylic acid.
mp 144° - 147° C (decomp.)
IR (KBr): 1760 cm$^{-1}$ (d) 7-[D(—)-α-amino-m-chloro-p-ethoxycarbonyloxyphenylacetamido]-3-(1,3,4-thiadiazol-2-yl-thiomethyl)-3-cephem-4-carboxylic acid trifluoro acetate.
mp 132° - 135° C (decomp.)
IR (KBr): 1770 cm$^{-1}$ (e) 7-[D(—)-α-(4-ethyl-2,3-dioxopiperazin-1-yl-carbonylamino)-m-chloro-p-ethoxycarbonyloxyphenylacetamido]-3-(1,3,4-thiadiazol-2-yl-thiomethyl)-3-cephem-4-carboxylic acid
mp 149° - 152° C (decomp.)
IR (KBr): 1780 (β-lactam), 1720 - 1650 cm$^{-1}$
UV λmax: 264 nm. (methanol)

EXAMPLE 7

7-[D(—)-α-(4-ethyl-2,3-dioxopiperazin-1-yl-carbonylamino-m-chloro-p-hydroxyphenylacetamido]-3-(5-methyl-1,3,4-thiadiazol-2-yl-thiomethyl)-3-cephem-4-carboxylic acid:

Instead of 7-amino-3-(1,3,4-thiadiazol-2-yl-thiomethyl)-3-cephem-4-carboxylic acid used in Example 1, 7-amino-3-(5-methyl-1,3,4-thiadiazol-2-yl-thiomethyl)-3-cephem-4-carboxylic acid was used and treated in a similar manner to that of Example 1.

The object compound was obtained in 78% yield.
IR (KBr): 1765 cm$^{-1}$ (β-lactam)
UV λmax: 272 nm. (ethanol)
MIC value against Pseudomonas aeruginosa C-73-2: 12.5 mcg/ml.
mp. 157° - 162° C (decomp.)

EXAMPLE 8

7-[D(—)-α-(4-ethyl-2,3-dioxopiperazin-1-yl-carbonylamino)-p-hydroxyphenylacetamido]-3-(5-methyl-1,3,4-thiadiazol-2-yl-thiomethyl)-3-cephem-4-carboxylic acid:

Instead of 7-amino-3-(1,3,4-thiadiazol-2-yl-thiomethyl)-3-cephem-4-carboxylic acid used in Example 2, 7-amino-3-(5-methyl-1,3,4-thiadiazol-2-yl-thiomethyl)-3-cephem-4-carboxylic acid was used and treated in a similar manner to that of Example 2 to obtain the object compound.
IR (KBr): 1780 cm$^{-1}$ (β-lactam)
UV λmax: 265 nm. (ethanol)
MIC value against Pseudomonas aeruginosa C-73-2: 25 mcg/ml.

EXAMPLE 9

7-[D(—)-α-(4-ethyl-2,3-dioxopiperazin-1-yl-carbonylamino)-p-acetoacetoxyphenylacetamido]-3-(1,3,4-thiadiazol-2-yl-thiomethyl)-3-cephem-4-carboxylic acid:

647 mg(1 m mol.) of 7-[D(—)-α-(4-ethyl-2,3-dioxopiperazinl-yl-carbonylamino)-p-hydroxyphenylacetamido]-3-(1,3,4-thiadiazol-2-yl-thiomethyl)-3-cephem-4-carboxylic acid were suspended in a mixture of 5 ml of ethyl acetate and 5 ml of water. To this suspension was added dropwise an aqueous solution containing 1 m mol. of sodium carbonate with stirring under ice-cooling and a clear solution was obtained. A methylene chloride solution containing 2 m mol. of diketene was slowly added dropwise to this solution and allowed to react for 30 minutes with stirring under ice-cooling. The reaction was monitored by thin layer chromatography. After the reaction was completed, the aqueous layer was separated, to which ethyl acetate was added followed by the adjustment to a pH of about 3.0 with an aqueous 50% phosphoric acid solution. The ethyl acetate layer was separated, washed with water, dried and then the solvent was removed under reduced pressure to obtain the object compound a solid in a 73% yield.
IR (KBr) : 1780 cm$^{-1}$
UV λmax : 264 nm. (methanol)
MIC against Pseudomonas aeruginosa E2: 6.25 mcg/ml

EXAMPLE 10

7-[D(—)-α-(4-ethyl-2,3-dioxopiperazin-1-yl-carbonylamino)-m-chloro-p-acetoacetoxy-phenylacetamido]-3-(1,3,4-thiadiazol-2-yl-thiomethyl)-3-cephem-4-carboxylic acid:

Instead of 7-[D(—)-α-(4-ethyl-2,3-dioxopiperazin-1-yl-carbonylamino)-p-hydroxyphenylacetamido]-3-(1,3,4-thiadiazol-2-yl-thiomethyl)-3-cephem-4-carboxylic acid used in Example 9, 7-[D(—)-α-(4-ethyl-2,3-dioxopiperazin-1-yl-carbonylamino)-m-chloro-p-hydroxyphenylacetamido]-3-(1,3,4-thiadiazol-2-yl-thiomethyl)-3-cephem-4-carboxylic acid was used and treated in a similar manner to Example 9 to obtain the object compound. Yield: 70%.

IR (KBr) : 1780 cm$^{-1}$
UV λmax : 264 nm. (methanol)
MIC against Pseudomonas aeruginosa E2 : 3.13 mcg/ml.

EXAMPLES 11 – 12

Instead of 1,3,4-thiadiazol-2-thiol used in Example 5 and Example 6, 5-methyl-1,3,4-thiadiazol-2-thiol was used and treated in a similar manner to that of Example 5 and Example 6 respectively. The following compounds were obtained.

(11) 7-[D(—)-α-(4-ethyl-2,3-dioxopiperazin-1-yl-carbonylamino)-p-ethoxycarbonyloxyphenylacetamido]-3-(5-methyl-1,3,4-thiadiazol-2-yl-thiomethyl)-3-cephem-4-carboxylic acid.

mp 147° – 157° C (decomp.)
IR (KBr) : 1765 cm$^{-1}$
UV λmax : 268 nm. (95% ethanol)
MIC against Pseud. aeruginosa E2 : 12.5 mcg/ml

(12) 7-[D(—)-α-(4-ethyl-2,3-dioxopiperazin-1-yl-carbonylamino)-m-chloro-p-ethoxycarbonyloxyphenylacetamido]-3-(5-methyl-1,3,4-thiadiazol-2-yl-thiomethyl)-3-cephem-4-carboxylic acid.

mp 147 – 152° C (decomp.)
IR (KBr) : 1765 cm$^{-1}$
UV λmax : 267 nm. (95% ethanol)
MIC against Pseud. aeug. E2 : 12.5 mcg/ml

EXAMPLES 13 – 14

Instead of 1,3,4-thiadiazol-2-thiol and ethyl chlorocarbonate used in Example 5 and 6, 5-methyl-1,3,4-thiadiazol-2-thiol and acetyl chloride were used and treated in a similar manner to that of Example 5 and 6 respectively. The following compounds were obtained.

(13) 7-[D(—)-α-(4-ethyl-2,3-dioxopiperazin-1-yl-carbonylamino)-p-acetoxyphenylacetamido]-3-(5-methyl-1,3,4-thiadiazol-2-yl-thiomethyl)-3-cephem-4-carboxylic acid.

(14) 7-[D(—)-α-(4-ethyl-2,3-dioxopiperazin-1-yl-carbonylamino)m-chloro-p-acetoxyphenylacetamido]-3-(5-methyl-1,3,4-thiadiazol-2-yl-thiomethyl)-3-carboxylic acid.

EXAMPLES 15 – 16

Instead of 7-[D(—)-α-(4-ethyl-2,3-dioxopiperazin-1-yl-carbonylamino)-p-hydroxyphenylacetamido]-3-(1,3,4-thiadiazol-2-yl-thiomethyl)-3-cephem-4-carboxylic acid used in Example 9, 7-[D(—)-α-(4-ethyl-2,3-dioxopiperazin-1-yl-carbonylamino)-p-hydroxyphenylacetamido]-3-(5-methyl-1,3,4-thiadiazol-2-yl-thiomethyl)-3-cephem-4-carboxylic acid was used and treated in a similar manner to that of Example 9.

7-[D(—)-α-(4-ethyl-2,3-dioxopiperazin-1-yl-carbonylamino)p-acetoacetoxyphenylacetamido]-3-(5-methyl-1,3,4-thiadiazol-2-yl-thiomethyl)-3-cephem-4-carboxylic acid was obtained.

The corresponding m-chloro compound was obtained in the same way.

EXAMPLE 17

7-[D(—)-α-(4-ethyl-2,3-dioxopiperazin-1-yl-carbonylamino)-p-iso-butoxycarbonyloxyphenylacetamido]-3-(1,3,4-thiadiazol-2-yl-thiomethyl)-3-cephem-4-carboxylic acid:

Instead of ethyl chlorocarbonate used in Example 5, isobutyl chlorocarbonate was used and treated in a similar manner to that of Example 5. The object compound was obtained in a 77% yield.

mp 144° – 148° C (decomp.)
IR (KBr) : 1765 cm$^{-1}$ (β:lactam)
UV λmax : 267 nm.
MIC against Pseud. aerug. E2: 12.5 mcg/ml

EXAMPLE 18

Instead of 4-ethyl-2,3-dioxopiperazin-1-yl-carbonyl chloride used in Example 5-e),

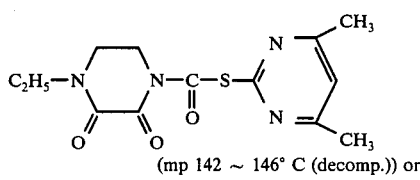

(mp 142 ~ 146° C (decomp.)) or

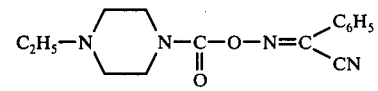

was used and treated in a similar manner to that of Example 5 – e) to give the object compound in 50 – 80% yield.

The product was identified with that obtained in Example 5.

What is claimed is:

1. A D(—)-isomer of a compound of the formula (I):

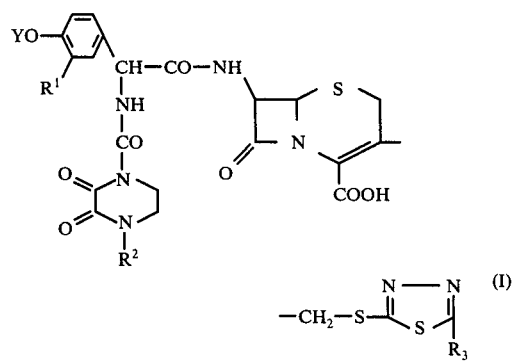

wherein Y is hydrogen lower aliphatic acyl, lower alkoxycarbonyl or acetylmethylcarbonyl, R$^1$ is hydrogen or halogen, R$^2$ is lower alkyl and R$^3$ is hydrogen or lower alkyl, and pharmaceutically acceptable salts thereof.

2. A compound as claimed in claim 1, wherein the pharmaceutically acceptable salt is an alkali metal salt.

3. A compound as claimed in claim 1, wherein the pharmaceutically acceptable salt is the sodium or potassium salt.

4. 7-[D(—)-α-(4-ethyl-2,3-dioxopiperazin-1-yl-carbonylamino)-p-ethoxycarbonyloxyphenylacetamido]-3-(1,3,4-thiadiazol-2-yl-thiomethyl)-3-cephem-4-carboxylic acid as claimed in claim 1.

5. 7-[D(—)-α-(4-ethyl-2,3-dioxopiperazin-1-yl-carbonylamino)-m-chloro-p-ethoxycarbonyloxyphenylacetamido]-3-(1,3,4-thiadiazol-2-yl-thiomethyl)-3-cephem-4-carboxylic acid as claimed in claim 1.

6. 7-[D(—)-α-(4-ethyl-2,3-dioxopiperazin-1-yl-carbonylamino)-p-acetoxyphenylacetamido]-3-(1,3,4-thiadiazol-2-yl-thiomethyl)-3-cephem-4-carboxylic acid as claimed in claim 1.

7. 7-[D(—)-α-(4-ethyl-2,3-dioxopiperazin-1-yl-carbonylamino)-m-chloro-p-acetoxyphenylacetamido]-3-(1,3,4-thiadiazol-2-yl-thiomethyl)-3-cephem-4-carboxylic acid as claimed in claim 1.

8. 7-[D(—)-α-(4-ethyl-2,3-dioxopiperazin-1-yl-carbonylamino)-p-hydroxyphenylacetamido]-3-(1,3,4-thiadiazol-2-yl-thiomethyl)-3-cephem-4-carboxylic acid as claimed in claim 1.

9. 7-[D(—)-α-(4-ethyl-2,3-dioxopiperazin-1-yl-carbonylamino)-m-chloro-p-hydroxyphenylacetamido]-3-(1,3,4-thiadiazol-2-yl-thiomethyl)-3-cephem-4-carboxylic acid as claimed in claim 1.

10. 7-[D(—)-α-(4-ethyl-2,3-dioxopiperazin-1-yl-carbonylamino)-p-acetoacetoxyphenylacetamido]-3-(1,3,4-thiadiazol-2-yl-thiomethyl)-3-cephem-4-carboxylic acid as claimed in claim 1.

11. 7-[D(—)-α-(4-ethyl-2,3-dioxopiperazin-1-yl-carbonylamino)-m-chloro-p-acetoacetoxyphenylacetamido]-3-(1,3,4-thiadiazol-2-yl-thiomethyl)-3-cephem-4-carboxylic acid as claimed in claim 1.

12. 7-[D(—)-α-(4-ethyl-2,3-dioxopiperazin-1-yl-carbonylamino)-p-iso-butoxycarbonyloxyphenylacetamido]-3-(1,3,4-thiadiazol-2-yl-thiomethyl)-3-cephem-4-carboxylic acid as claimed in claim 1.

13. 7-[D(—)-α-(4-ethyl-2,3-dioxopiperazin-1-yl-carbonylamino)-p-ethoxycarbonyloxyphenylacetamido]-3-(5-methyl-1,3,4-thiadiazol-2-yl-thiomethyl)-3-cephem-4-carboxylic acid as claimed in claim 1.

14. 7-[D(—)-α-(4-ethyl-2,3-dioxopiperazin-1-yl-carbonylamino)-m-chloro-p-ethoxycarbonyloxyphenylacetamido]-3-(5-methyl-1,3,4-thiadiazol-2-yl-thiomethyl)-3-cephem-4-carboxylic acid as claimed in claim 1.

15. 7-[D(—)-α-(4-ethyl-2,3-dioxopiperazin-1-yl-carbonylamino)-p-hydroxyphenylacetamido]-3-(5-1,3,4-thiadiazol-2-yl-thiomethyl)-3-cephem-4-carboxylic acid as claimed in claim 1.

16. 7-[D(—)-α-(4-ethyl-2,3-dioxopiperazin-1-yl-carbonylamino)-m-chloro-p-hydroxyphenylacetamido]-3-(5-methyl-1,3,4-thiadiazol-2-yl-thiomethyl)-3-cephem-4-carboxylic acid as claimed in claim 1.

17. A pharmaceutical composition having antibacterial activity which comprises an effective amount of a compound as claimed in claim 1 and a pharmaceutically acceptable carrier therefor.

* * * * *

Notice of Adverse Decision in Interference

In Interference No. 100,406, involving Patent No. 4,103,008, I. Toshiyasu, H. Minoru, H. Mariko and N. Hazime, 7[2(2,3-DIOXOPIPERAZIN-1-YL-CARBONYLAMINO) SUBSTITUTED 2 PHENYL-ACETAMIDO]-3-2'-THIADIAZOLYL CEPHALOSPORANIC ACID DERIVATIVES, final judgment adverse to the patentees was rendered November 24, 1981, as to claims 1-3, 8, 15 and 17.

[*Official Gazette February 23, 1982.*]